US011039855B2

(12) United States Patent
Darrow et al.

(10) Patent No.: US 11,039,855 B2
(45) Date of Patent: Jun. 22, 2021

(54) GUIDE INSERTS FOR INSERTABLE MEDICAL TOOLS AND ASSOCIATED METHOD THEREOF

(71) Applicant: GENERAL ELECTRIC COMPANY, Schenectady, NY (US)

(72) Inventors: Robert David Darrow, Scotia, NY (US); Ileana Hancu, Clifton Park, NY (US); Eric William Fiveland, Niskayuna, NY (US)

(73) Assignee: General Electric Company, Schenectady, NY (US)

( * ) Notice: Subject to any disclaimer, the term of this patent is extended or adjusted under 35 U.S.C. 154(b) by 334 days.

(21) Appl. No.: 16/002,486

(22) Filed: Jun. 7, 2018

(65) Prior Publication Data
US 2018/0280054 A1  Oct. 4, 2018

Related U.S. Application Data

(62) Division of application No. 14/620,034, filed on Feb. 11, 2015, now abandoned.

(51) Int. Cl.
*A61B 17/34* (2006.01)
*A61B 10/02* (2006.01)
*A61B 17/00* (2006.01)
*A61B 90/11* (2016.01)

(52) U.S. Cl.
CPC .......... *A61B 17/3403* (2013.01); *A61B 10/02* (2013.01); *A61B 90/11* (2016.02); *A61B 2017/00526* (2013.01); *A61B 2017/3411* (2013.01)

(58) Field of Classification Search
CPC ........ A61B 17/3403; A61B 2017/3407; A61B 2017/3411; A61B 10/02; A61B 90/11
See application file for complete search history.

(56) References Cited

U.S. PATENT DOCUMENTS

| 6,254,614 | B1* | 7/2001 | Jesseph | A61B 6/0414 600/562 |
| 6,902,569 | B2* | 6/2005 | Parmer | A61B 90/11 606/108 |
| 9,681,919 | B2* | 6/2017 | Glossop | A61B 90/11 |
| 9,730,762 | B2* | 8/2017 | Abdelsalam | A61B 17/3403 |
| 2004/0167543 | A1* | 8/2004 | Mazzocchi | A61B 90/11 606/130 |
| 2008/0200798 | A1 | 8/2008 | Eklund et al. | |

(Continued)

OTHER PUBLICATIONS

Larson et al., "Design of an MRI-Compatible Robotic Stereotactic Device for Minimally Invasive Interventions in the Breast.", Journal of Biomechanical Engineering, vol. 126. issue 4, pp. 458-465, Aug. 2004.

(Continued)

*Primary Examiner* — Devin B Henson (57) ABSTRACT

A guide insert for use in insertion of a medical tool into a patient and an associated method of using the guide insert in a medical device are disclosed. The guide insert includes a base sized and shaped to be inserted into an opening of a grid of the medical device, a rotatable structure configured to fit on or within the base, and a securing cap configured to secure the rotatable structure to the base and to prevent rotation of the rotatable structure when secured.

16 Claims, 11 Drawing Sheets

(56) References Cited

U.S. PATENT DOCUMENTS

| | | | |
|---|---|---|---|
| 2009/0292244 A1 | 11/2009 | Flagle et al. | |
| 2010/0324448 A1* | 12/2010 | Mollere | A61B 90/11 |
| | | | 600/567 |
| 2011/0092850 A1* | 4/2011 | Kulkarni | A61B 90/17 |
| | | | 600/562 |
| 2015/0335316 A1 | 11/2015 | Darrow et al. | |

OTHER PUBLICATIONS

Taneja et al., Technical Note: MRI-Guided Breast Biopsy—Our Preliminary Experience, Indian Journal of Radiology and Imaging, vol. 20, Issue 3, pp. 218-220, 2010.

Kondor et al., "On Demand Additive Manufacturing of a Basic Surgical Kit", Journal of Medical Devices, vol. 7, Issue 3, Jul. 3, 2013.

* cited by examiner

GUIDE INSERTS FOR INSERTABLE MEDICAL TOOLS AND ASSOCIATED METHOD THEREOF

CROSS REFERENCE TO RELATED APPLICATIONS

This patent application is a divisional of U.S. Non-Provisional patent application Ser. No. 14/620,034 flied on Feb. 11, 2015, which is incorporated by reference herein in its entirely.

BACKGROUND

The subject matter disclosed herein relates to guides for use in interventional and navigation contexts for placement of a tool within a patient at a specific location and orientation.

Various medical procedures involve the insertion, and possible navigation, of a tool within a patient. One example of such a procedure is a biopsy procedure, in which a vacuum-assisted biopsy handpiece or biopsy needle is inserted into a patient with the purpose of placing an opening near the needle tip within or proximate to a growth from which a sample is to be taken. As will be appreciated, in such a procedure, the needle and, in particular the opening of the needle, must be placed accurately at the location to be biopsied to obtain the desired sample and to avoid unnecessary injury and trauma to the patient. As will be appreciated, other medical procedures may also work under similar constraints in terms of the need to place a device with great precision.

In terms of the procedure in question, other factors may complicate the operation. For example, certain imaging modalities that may be employed as part of the navigational procedure or preparation may limit the types of materials that may be employed in the vicinity of the scanner. For example, in X-ray based imaging modalities, the propensity of a given composition to reflect or absorb X-rays used in the imaging portion of the procedure may be a factor. Similarly, in magnetic resonance imaging applications, the strong magnetic fields involved in the imaging process may limit the types of materials that can be used in the vicinity of the scanner.

Further, in addition to the factors noted above, conventional techniques for guiding a tool (e.g., a needle) may be limited in terms of the flexibility provided for approaching the target area. For example, conventional guides used in a breast biopsy procedure may limit the approach to orientations perpendicular to the guide and to the grid in which the guide is inserted. Such an inflexible approach may limit a care givers ability to avoid intervening structures (such as vasculature) to reach the target area. Similarly, they are prevented from reaching structures outside the perimeter of the grid structure. As a result of these and other considerations, there is a need for improved mechanisms for guiding a tool, such as a biopsy needle, in certain procedures.

BRIEF DESCRIPTION

In one embodiment, a guide insert for use in insertion of a medical tool into a patent is provided. The guide insert includes a base sized and shaped to be inserted into an opening of a grid of a medical device, a rotatable structure configured to fit on or within the base, and a securing cap configured to secure the rotatable structure to the base and to prevent rotation of the rotatable structure when secured.

In another embodiment, a medical device is provided that includes a plate, a grid disposed facing the plate, a medical tool, and a guide insert positioned at least partially within an opening of a plurality of openings formed in the grid and configured for use in insertion of the medical tool into a patient. The guide insert includes a base sized and shaped to be inserted into the opening of the grid, a rotatable structure configured to fit on or within the base, and a securing cap configured to secure the rotatable structure to the base and to prevent rotation of the rotatable structure when secured.

In yet another embodiment, a method includes receiving an indication of a selected target region within a set of image data of a patient and determining a grid location in a grid for insertion of a guide insert based on the selected target region. Further, the method includes determining at least a guide channel orientation for the guide insert based on the selected target region and the grid location. The method additionally includes adjusting, without user intervention, a rotatable structure of the guide insert based on the determined guide channel orientation, where the rotatable structure defines at least a portion of a guide channel. Also, the method includes locking the rotatable structure to a base of the guide insert using a securing cap of the guide insert, at the determined guide channel orientation after the adjusting the rotatable structure.

In an additional embodiment, a method for configuring a medical tool guide is provided. In accordance with this method, an indication of a selected target region within a set of image data is received. Based on the selected target region, a grid location for insertion of a tool guide is determined. Based on the selected target region and the grid location, at least a guide channel orientation for the tool guide is determined. Based on the determined guide channel orientation, a rotatable component of the tool guide is adjusted, without user intervention. The rotatable structure defines at least a portion of the guide channel.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

One or more specific embodiments of the present invention will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements. Moreover, while the term "exemplary" may be used herein in connection to certain examples of aspects or embodiments of the presently disclosed technique, it will be appreciated that these examples are illustrative in nature and that the term "exemplary" is not used herein to denote any preference or requirement with respect to a disclosed aspect or embodiment. Further, any use of the terms "top," "bottom," "above," "below," other positional terms, and variations of these terms is made for convenience, but does not require any particular orientation of the described components.

The present approach relates to the manufacture and use of improved guides for use in the insertion of certain tools (including, but not limited to, MRI guided breast biopsy needles) into a patient. In one embodiment, a guide is fabricated or selected based on patient specific and/or navigational factors. For example, based on initial imaging for a given procedure, a guide may be custom fabricated (such as using additive manufacturing (e.g., 3-D printing) or subtractive manufacturing (e.g., numerically controlled milling)) for a given procedure so that the custom fabricated guide provides the desired angle of approach and depth based on the target region (e.g., a lesion) and intervening anatomy. Alternatively, a set of fabricated guides providing different angles of approach and/or depths may be provided as a set and the initial imaging may allow the caregiver to select an appropriate guide from t the set. In other embodiments, a guide may be provided that is adjustable, such as via a ball joint, and which may be adjusted (such as automatically or robotically) based on the initial imaging to the desired orientation.

Figure 1:
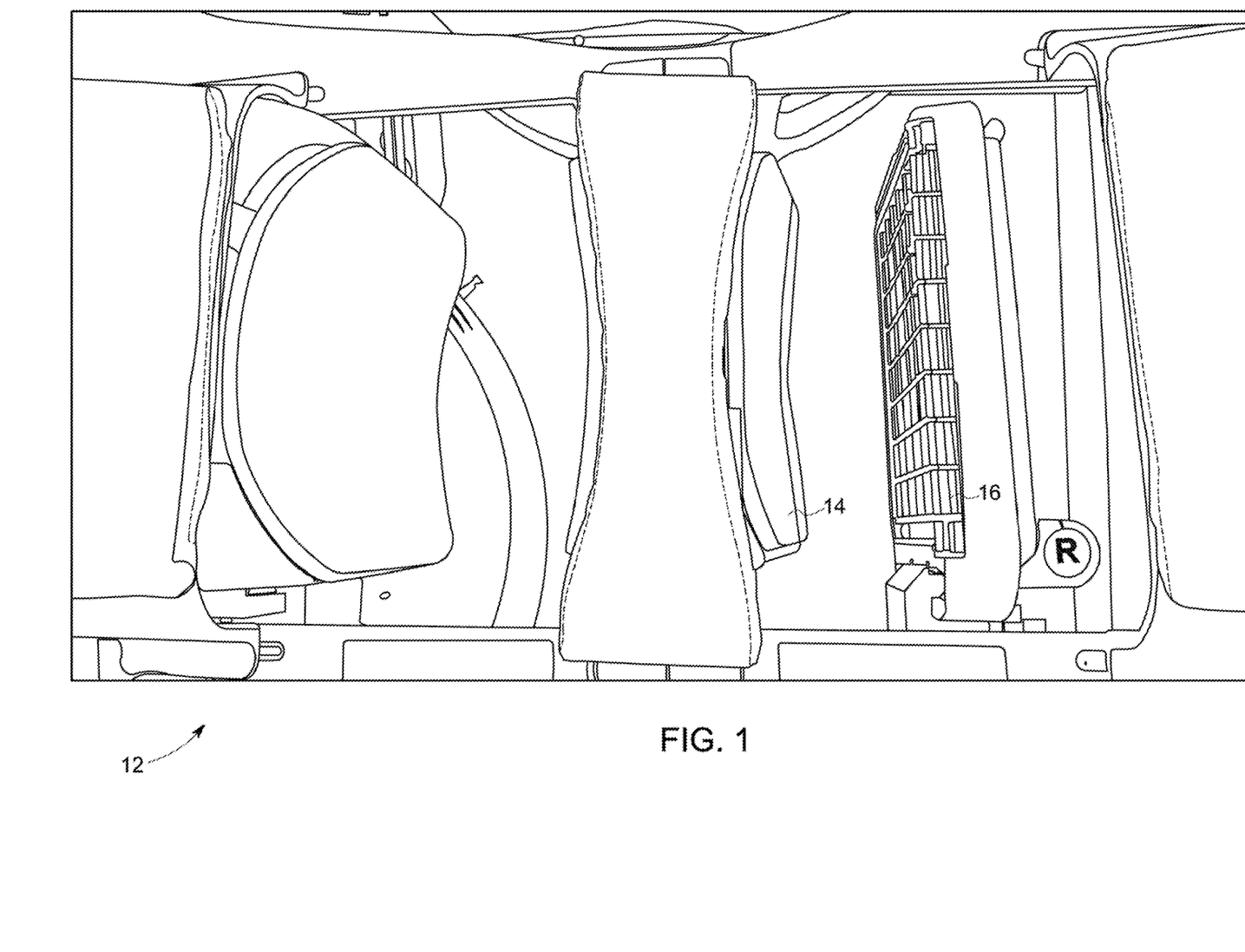
FIG. 1 depicts an imaging coil and biopsy grid, in accordance with aspects of the present disclosure.

With this in mind, an example of a conventional guide for use in a particular context (in this example, magnetic resonance imaging (MRI) guided breast biopsy) is discussed below to provide useful background context. Turning to FIG. 1, a magnetic resonance imaging (MRI) breast imaging coil 12 is depicted in which the patient's breast hangs pendant during imaging. In particular, the breast hangs pendant between an MR-compatible immobilization plate 14 and an MR-compatible biopsy grid 16, between which the breast is compressed during imaging.

The compressed breast is imaged, in this example using an MRI scanner to allow visualization of lesions present in the breast. An MRI contrast agent may be administered to the patient to facilitate this visualization process. A fiducial marker is used to localize the biopsy grid 16 relative to the lesion position(s), i.e., target region(s).

Figure 2:
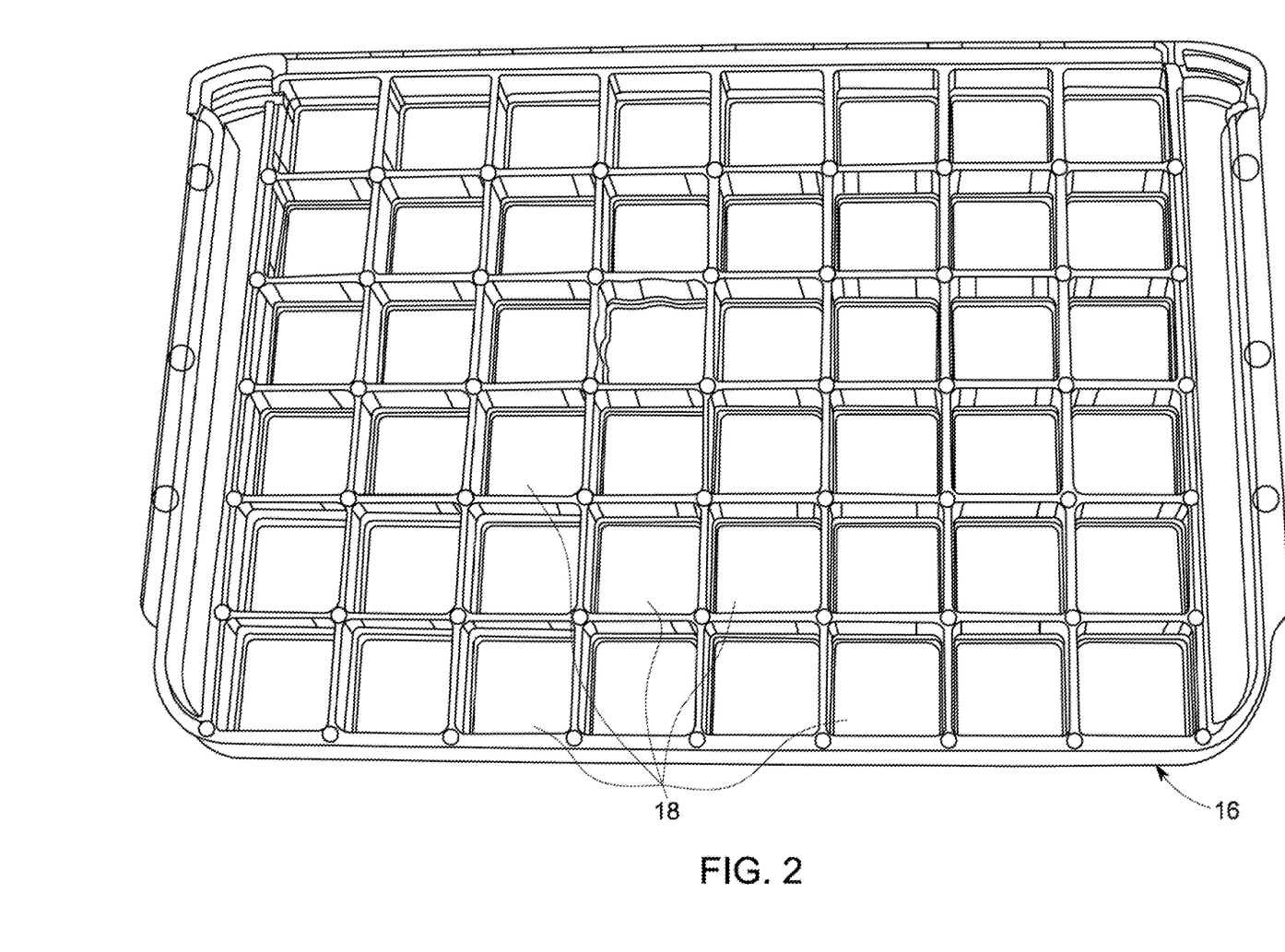
FIG. 2 depicts a biopsy grid, in accordance with aspects of the present disclosure.
Figure 3:
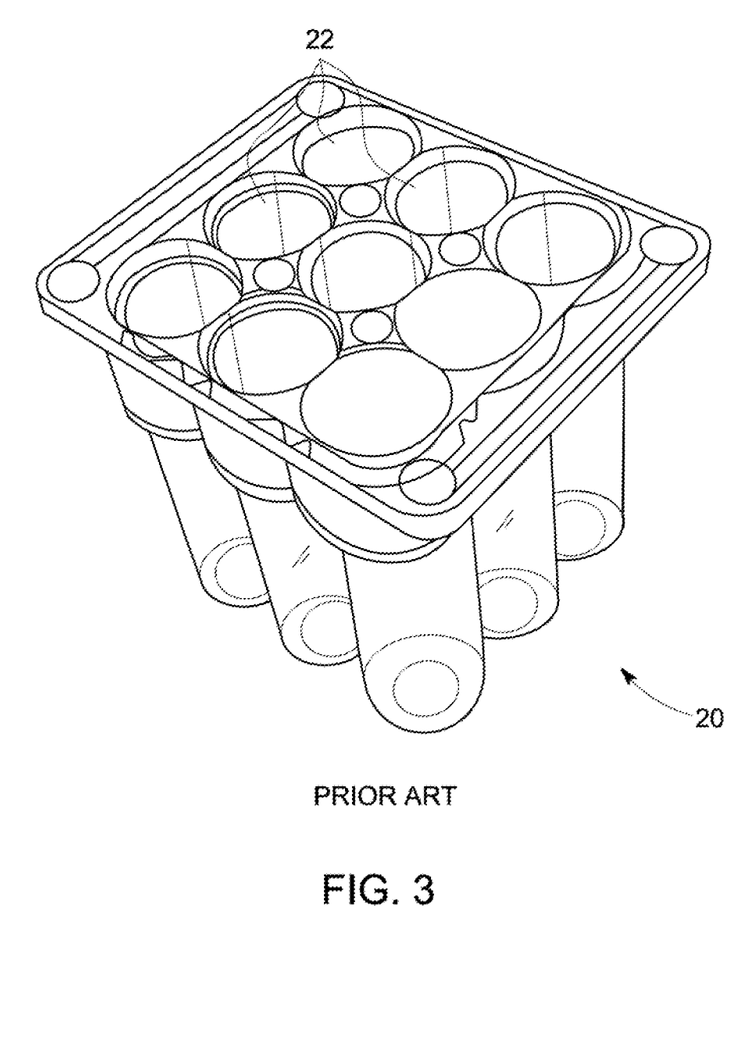
FIG. 3 depicts a conventional grid insert.

Prior to describing the use of the biopsy grid 16, the grid 16 and grid insert 20 are described in greater detail. Turning to FIG. 2, a top-down view of the biopsy grid 16 is provided. The open spaces 18 of the grid 16 are sized and shaped so as to allow insertion of a grid insert 20. A conventional grid insert 20 is shown in FIG. 3. Based on the prior imaging, a grid location (space 18) is selected for insertion of a grid insert 20. The grid insert 20 divides the space 18 into a set of insertion points for the tool to be inserted. By way of example, the depicted grid inset 20 is subdivided into a number of guide channels 22 sized to receive a tool (e.g., a biopsy needle) to be inserted or navigated within the patient.

Turning back to an interventional procedure, when imaging is complete, a lesion is selected, by a clinician, and one or more localization routines are executed (such as on the imaging system and/or other processor-based system) to compute the position of the selected lesion. The executed routines also compute the grid position (i.e., the appropriate opening or space 18) for the grid insert 20, the entry point (i.e., channel 22) within the grid insert 20 for the medical device, and the lesion depth.

As will be appreciated from the depiction of the insert 20, the channels 22 are oriented perpendicular to the primary surface of the insert 20 and grid 16. As a result, guidance of the tool is limited to positioning the tool, via the selected space 18 and channel 22 as close as possible over the target region using the grid 16 and insert 20, with no allowance made for intervening structures or alternative orientations (e.g., orientations other than perpendicular relative to the grid 16. Further, the accuracy of the tool localization relative to the target (e.g., lesion) region is limited to the resolution of the insertion points (i.e., channels 22) within the insert 20.

Figure 4:
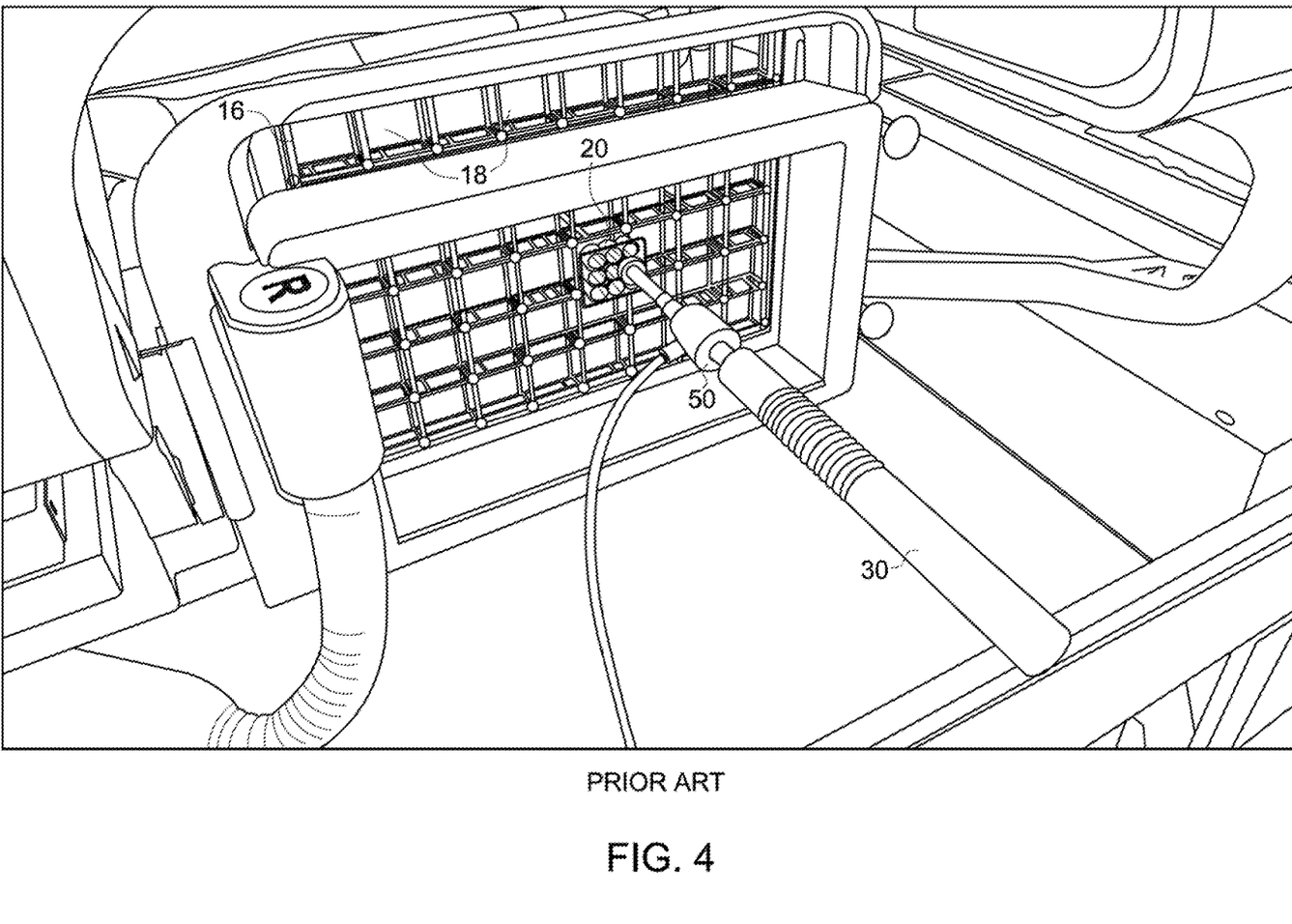
FIG. 4 depicts a conventional tool insertion using a biopsy grid and conventional grid insert.

An example, of this conventional arrangement can be seen in FIG. 4, where an insert 20 is positioned in a selected space 18 of a grid 16 and a tool 30 (here a stylet) is inserted into the selected channel 22 of the insert 20. Depth of insertion of the tool may be configured by a friction-fit ring on an introducer component 50 used to control insertion of the tool into the patient. As depicted, the needle 30 is limited to insertion orientations perpendicular to the grid 16 and insert 20. Thus it may be difficult to navigate around or avoid intervening structures or vasculature positioned between the target region and the grid 16.

With this in mind, the present approaches offer alternatives to the use of conventional grid inserts 20. In a first embodiment, instead of a conventional grid insert 20, a customized grid insert 50 (FIG. 5) is employed, where the grid insert 50 is customized with respect to the orientation and/or length of the provided shaft defining a hollow guide channel 52. As discussed herein, the orientation of the guide channel 52 may be characterized in terms of one or more of (1) guide channel angle with respect to the (x,y) dimensions of the grid insert 50 (i.e., the azimuth ($\omega$) herein)); (2) the guide channel angle in the z-dimension relative to the plane defined by the (x,y) dimensions defined by the grid insert 40 (i.e., the altitude ($\alpha$) herein); (3) guide channel offset (i.e., position) within the x,y plane of the insert 50; or (4) the length of the guide channel 52. That is, the orientation of the guide channel relative to the surface of the grid insert, and of the grid 16, is arbitrary and may be determined based on a given procedure, such that altitude, azimuth, and offset of the guide channel are determined or derived based on what is needed for the procedure, as opposed to being uniformly perpendicular relative to the insert. In addition, the exterior or interior of the guide channel 52 may be fabricated with threaded grooves to allow threaded association of one or more complementary threaded instruments with the guide channel 52.

Figure 5:
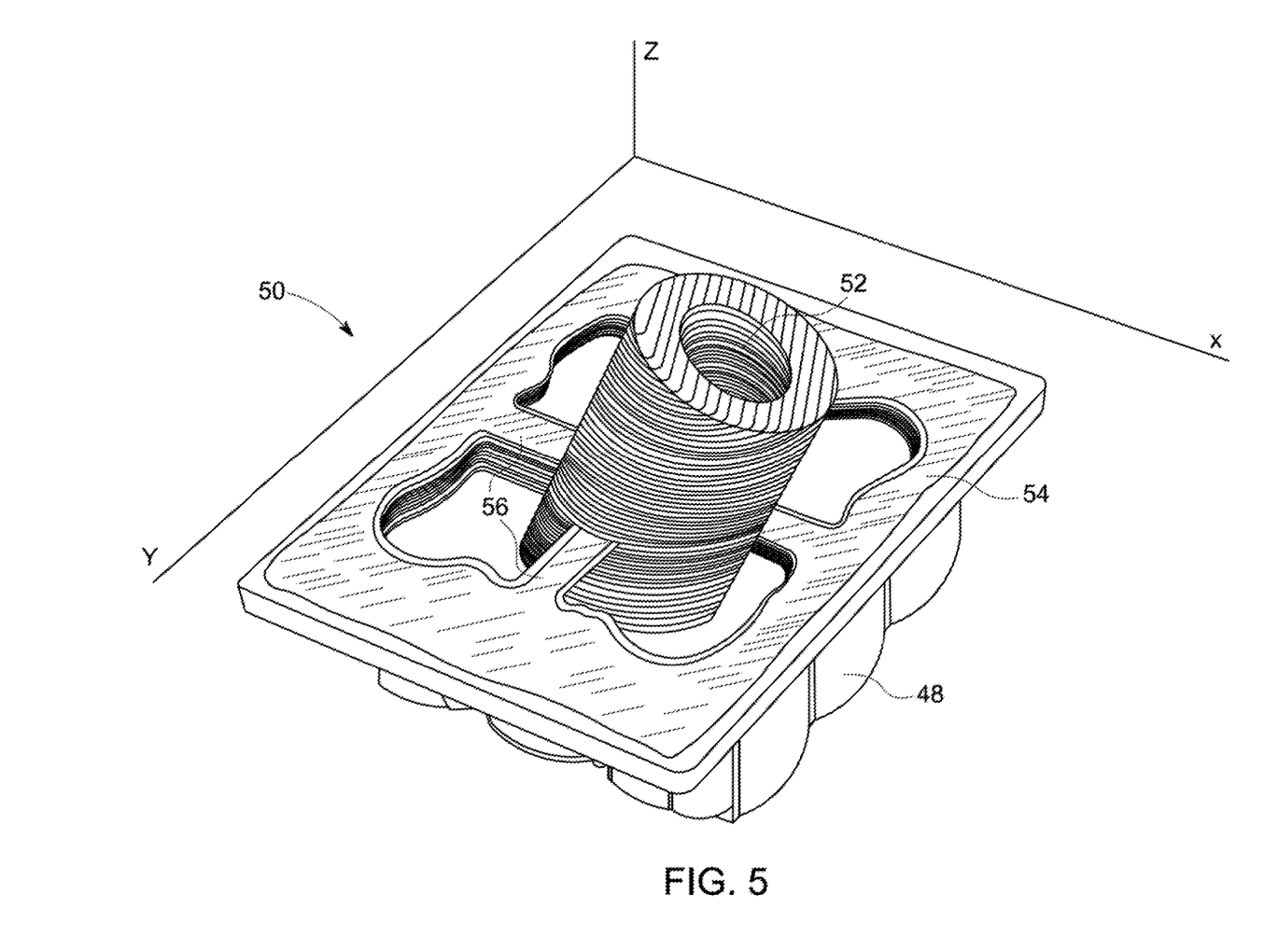
FIG. 5 depicts a grid insert, in accordance with aspects of the present disclosure.

In particular, in certain embodiments the grid insert 50 may be custom fabricated, such as at the facility where the procedure is being performed and while the patient is still fitted with the grid 16, such as using three-dimensional (3D) printing or other on-demand fabrication techniques. By way of example, the insert 50 may be custom fabricated using a medical grade plastic or other suitable composition from a 3D model generated by automated image analysis of the image data, which is then 3D printed on-site. Due to the heat associated with the fabrication process, the insert 50 may be sufficiently sterilized immediately after manufacture when in a clinical environment. Similarly, the grid insert may be fabricated from a pre-existing solid guide block by numerically controlled milling of the guide channel at the computed position and orientation.

In one such embodiment, the grid insert 50 is fabricated, with a single shaft defining a hollow guide channel 52 at an x,y offset (i.e., position), altitude, and azimuth determined by the automated analysis of the imaging data to guide a tool (e.g., a biopsy needle) to the target location when the customized grid insert is positioned within a specified grid space 18. In certain implementations, the guide channel 52 is fabricated to have an offset, azimuth and altitude that are computed (such as using one or more automated routines) based on the selected lesion position within the images with respect to a selected grid opening 18, which may also be selected or determined by the automated routines based upon the selected lesion position. In addition, the guide channel 52 may be customized in terms of length so as to also guide or limit the insertion depth of the tool when the custom guide 50 is employed.

As with other inserts, the grid insert 50 has a base 48 sized to fit within the openings 18 of the grid 16. The customized grid insert 50 may be fabricated to as to include an indication of the grid location 18 in which the insert 50 is to be inserted and/or markers to indicate the directional placement or facing of the insert 50 within the specified opening 18. Alternatively, in certain embodiments the insert 50 may be fabricated such that it fits within the grid openings 18 in only a single orientation (such as based on shape of the opening 18 and insert 50 or by employing a complementary cutout or feature on the grid 16 and insert 50 that must be matched to allow insertion), thus preventing insertion errors. In addition to, or instead of these approaches, a monitor or display may be employed to visually depict the proper placement and orientation of the custom insert 50 within the grid 16, thereby illustrating the correct placement and orientation of a given custom insert 50 within a grid 16 for a given procedure.

Figure 6:
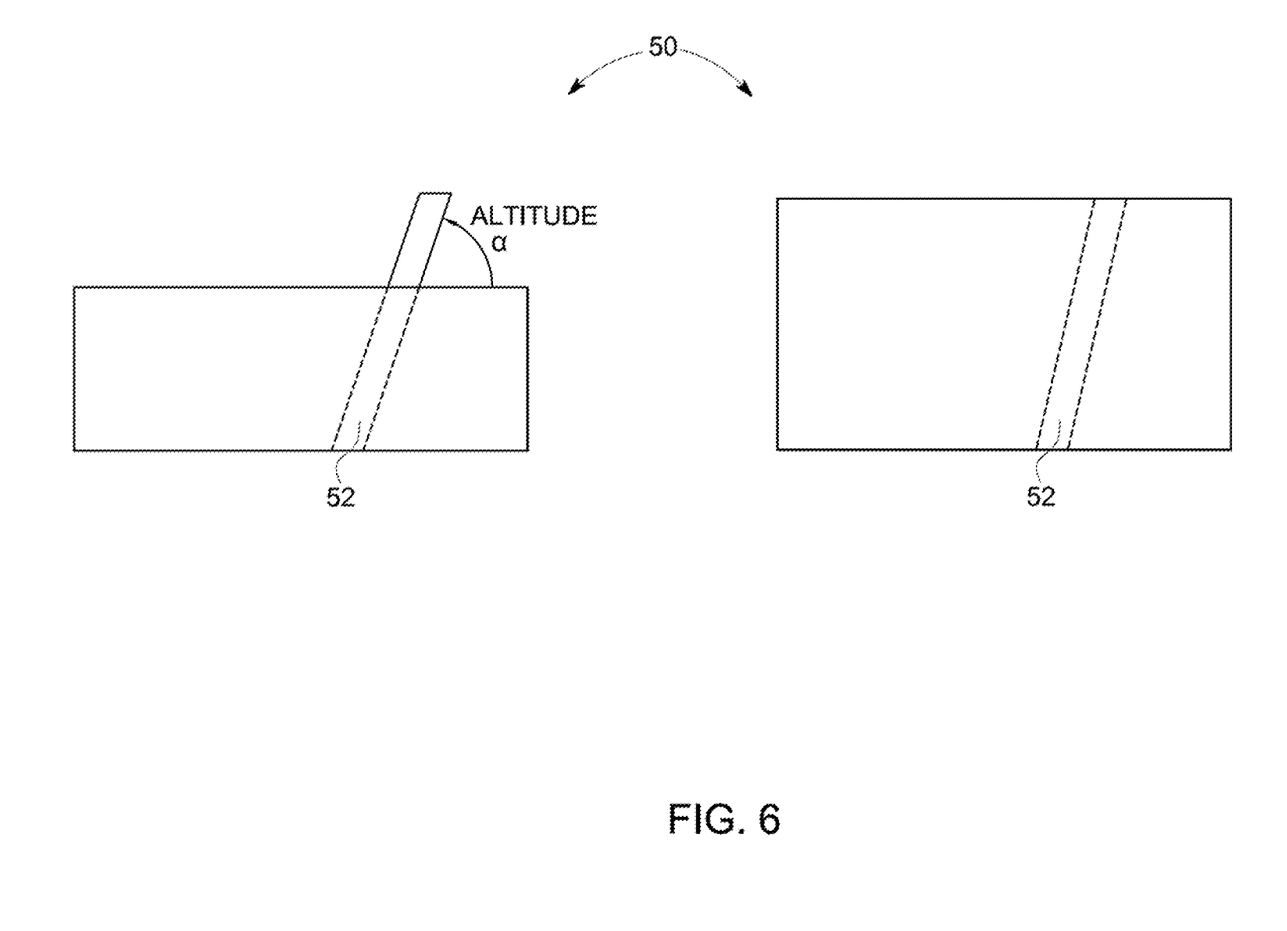
FIG. 6 depicts a side view of both a skeletal and block arrangement of a grid insert, in accordance with aspects of the present disclosure.

As depicted in FIG. 5, the insert 50 may be constructed as a skeletal framework having an outer ring 54 with one or more struts 56 extending from the ring 54 to the guide channel 52. Alternatively in other embodiments, the insert 50 may instead be fabricated as a block or mostly solid piece, with the hollow guide channel 52 being formed in the solid block and running through the insert 50. An example of one such arrangement is shown in FIG. 6, where a skeletal arrangement is shown from the side in the leftmost figure, and a comparable block arrangement is shown in the rightmost figure.

Figure 7:
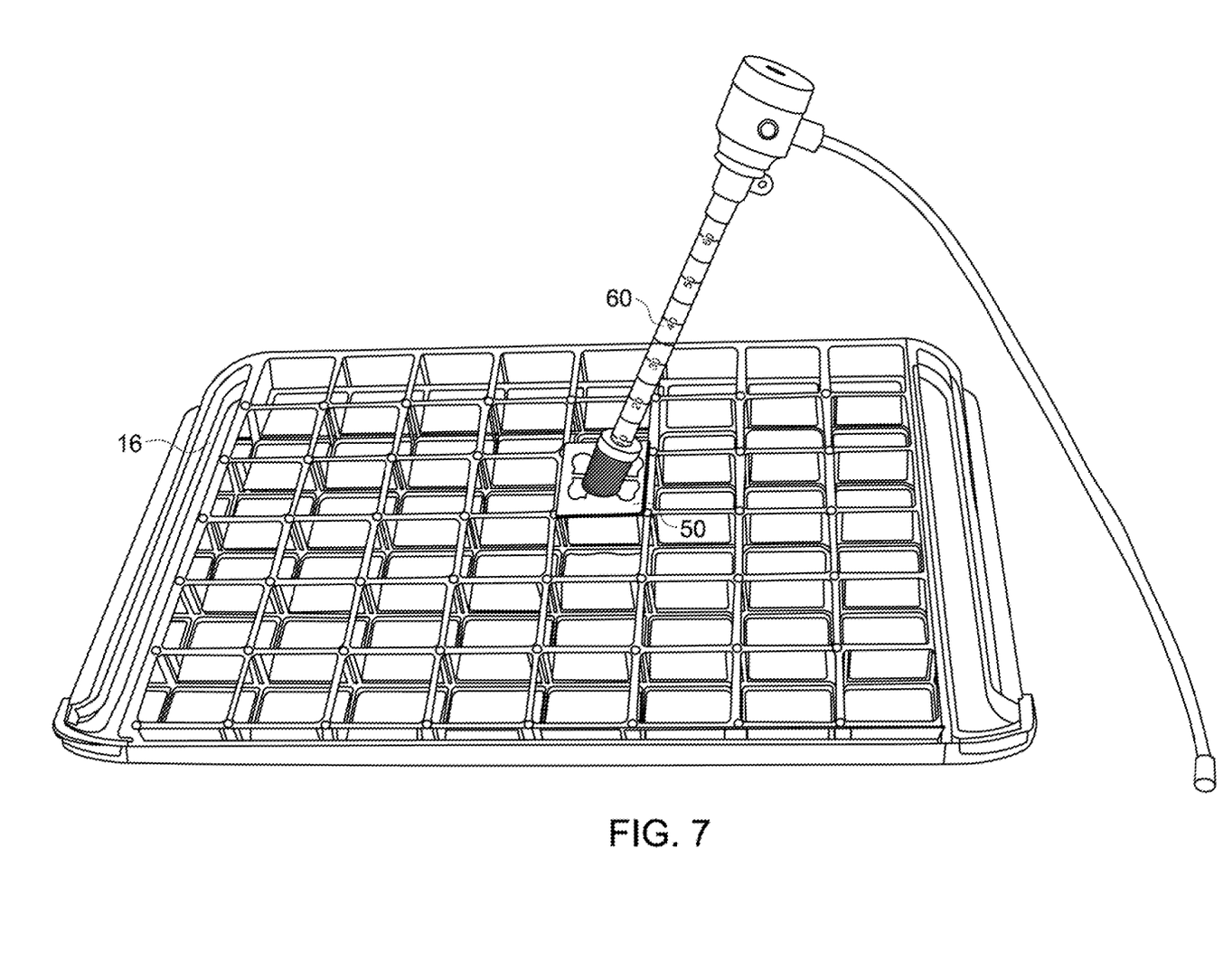
FIG. 7 depicts the grid insert of FIG. 5 in conjunction with a grid and introducer, in accordance with aspects of the present disclosure.

Turning to FIG. 7, an example, of a custom insert 50 is shown with a tool introducer 60 inserted into the guide channel that is angled relative to the surface of the insert 50 and relative to the grid 16. In this manner, a guide channel is provided that allows tool insertions at arbitrary, including non-perpendicular angles, relative to the grid 16 and where the guide channel may be precisely oriented and positioned within the selected grid opening 18. This allows vasculature or other intervening tissue or structures between the grid 16 and target region (e.g., lesion) to be avoided or, if not avoided, for the damage to such tissues to be reduced relative to conventional approaches.

Alternatively, instead of custom-fabricating an insert 50 for each procedure, a set of inserts 50, each having guide channels 52 at different offsets, altitudes, and azimuths may be provided. In such an implementation, the automated analysis of the image data may instead specify which insert 50 from among the set of differing inserts should be employed for a given procedure and may specify the grid opening 18 for insertion of the specified insert 50 and the orientation of the insert 50 within the opening 18. In the event no pre-fabricated insert 50 is suitable for a given procedure, a custom insert 50 may be fabricated and used as discussed above and, after use in the procedure, may be used to supplement the previous set of inserts.

While the preceding embodiments relate to the fabrication and use of custom inserts 50, in other implementations an insert 80 may be provided in which the orientation of the hollow guide channel is adjustable so that a given insert may be adjusted to have a different guide channel orientation based on the pre-procedure imaging.

Figure 8:
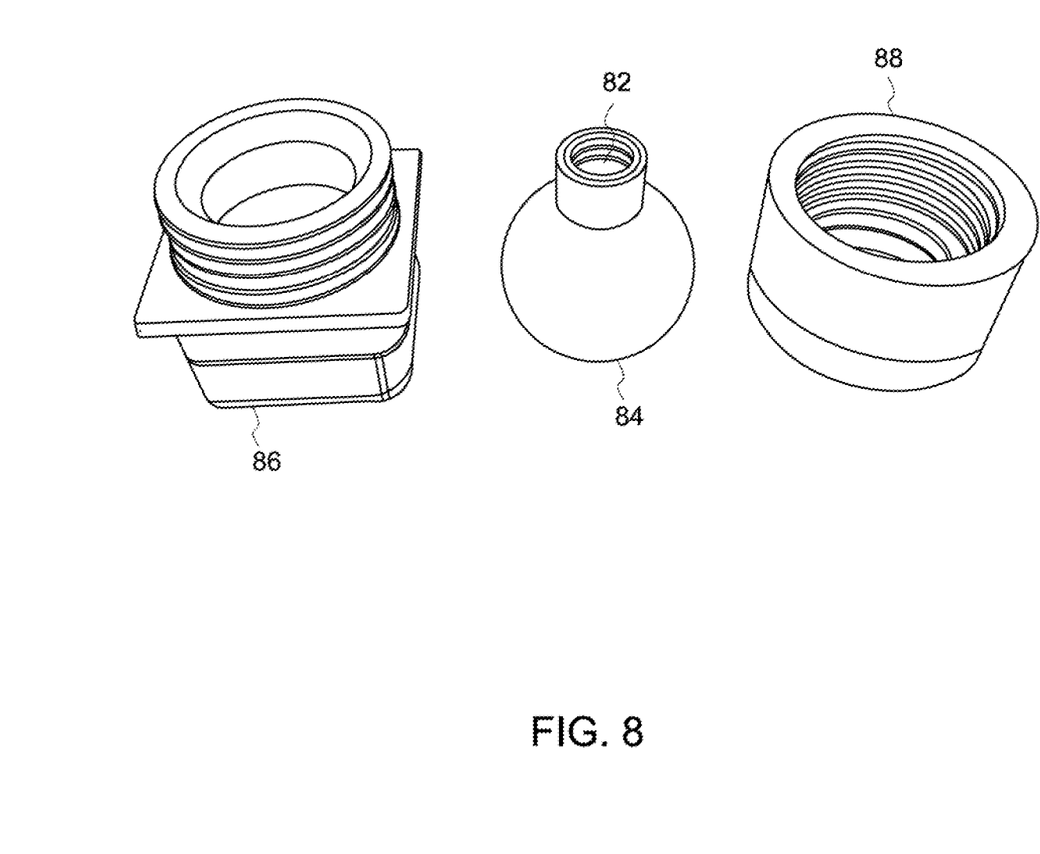
FIG. 8 depicts unassembled components of an adjustable grid insert, in accordance with aspects of the present disclosure.
Figure 9:
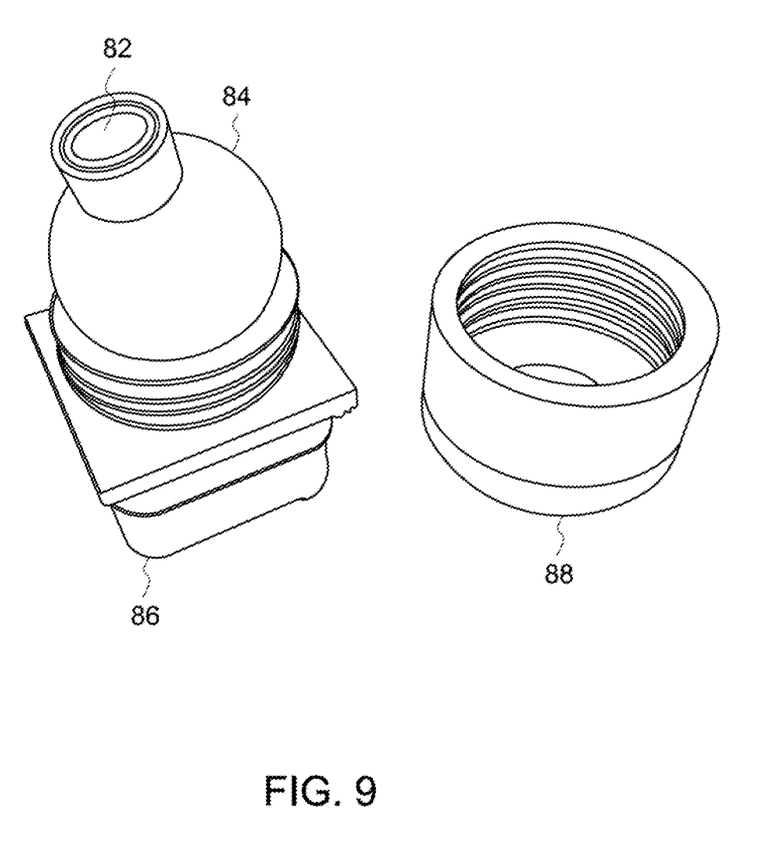
FIG. 9 depicts partially-assembled components of an adjustable grid insert, in accordance with aspects of the present disclosure.
Figure 10:
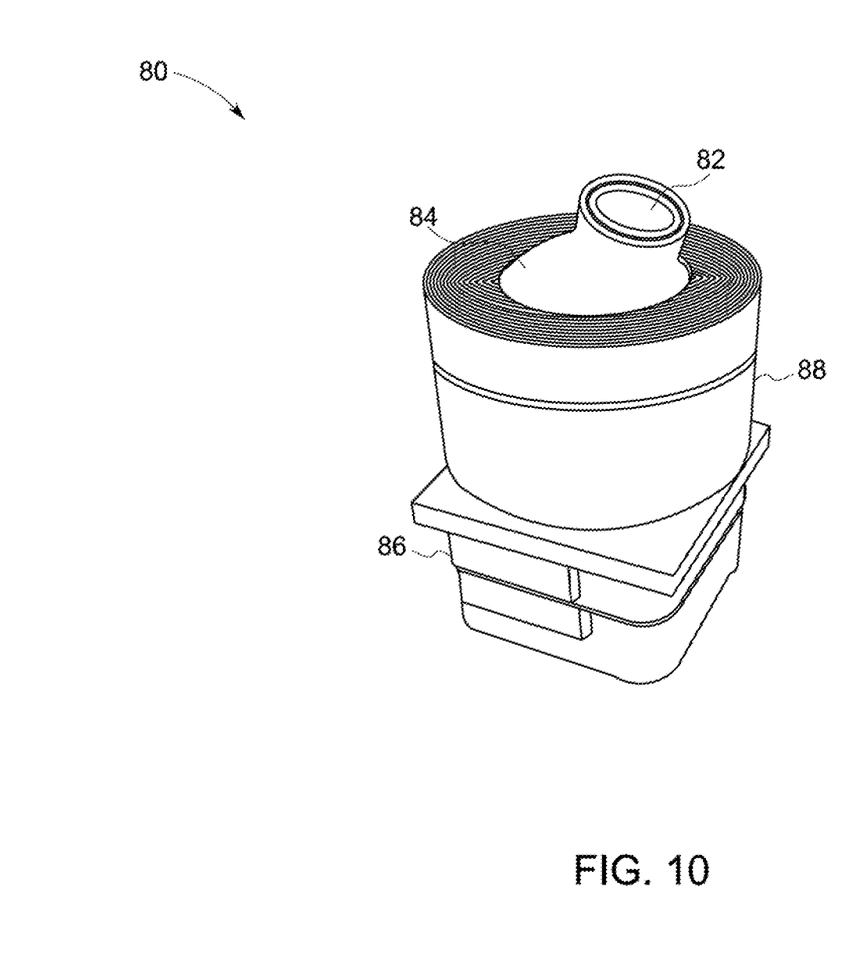
FIG. 10 depicts an assembled adjustable grid insert, in accordance with aspects of the present disclosure.

By way of example, and turning to FIGS. 8-10, the guide channel 82 may be provided as part of a shaft or hole defined in or on a ball structure or other rotatable structure 84. In such an embodiment, the rotatable structure 84 may be positioned within a conforming base 86 configured to be positioned within an opening 18 of the grid 16. A securing cap 88 may be secured to the base 86 (such as via a threaded groove) so as to hold the rotatable structure 84 in place and to lock the orientation of the rotatable structure 84 when tightened. FIG. 8 depicts the unassembled components of such an insert 80; FIG. 9 depicts the partially assembled components of such an insert 80; and FIG. 10 depicts the assembled insert 80.

In one implementation, an adjustable insert 80 may be manually or robotically configured (i.e., the guide channel 82 may be oriented in terms of altitude and azimuth relative to the base 86 and/or specified grid opening) based upon an automated analysis of the image data. In this manner, the executed routines may determine a grid opening 18 and guide channel orientation. (i.e., altitude and azimuth) based upon the target region (e.g., lesion) specified by the caregiver. An adjustable insert 80 may then be configured (i.e., the guide channel 82 and rotatable structure 84 may be oriented) so that, when the adjusted insert 80 is inserted in the proper orientation within the specified opening, the guide channel 82 will direct an inserted tool to the target region. When oriented by the robotic system based upon the determined guide channel altitude and azimuth, the robotic system may, securely lock the rotatable structure 84 in place to prevent additional or accidental change to the orientation of the guide channel 82, such as using one or more locking or securement features provided on the insert 80.

In certain implementations the shaft defining the guide channel 82 may have an adjustable length (e.g., a telescoping or otherwise adjustable length) that may be adjusted as part of the configuration process to limit the depth of insertion of the tool. Alternatively, ball structures 84 having different shaft length may be provided and a ball structure having the specified shaft length may be provided to the assembly system for configuration and orientation by the robotic or automated system.

Figure 11:
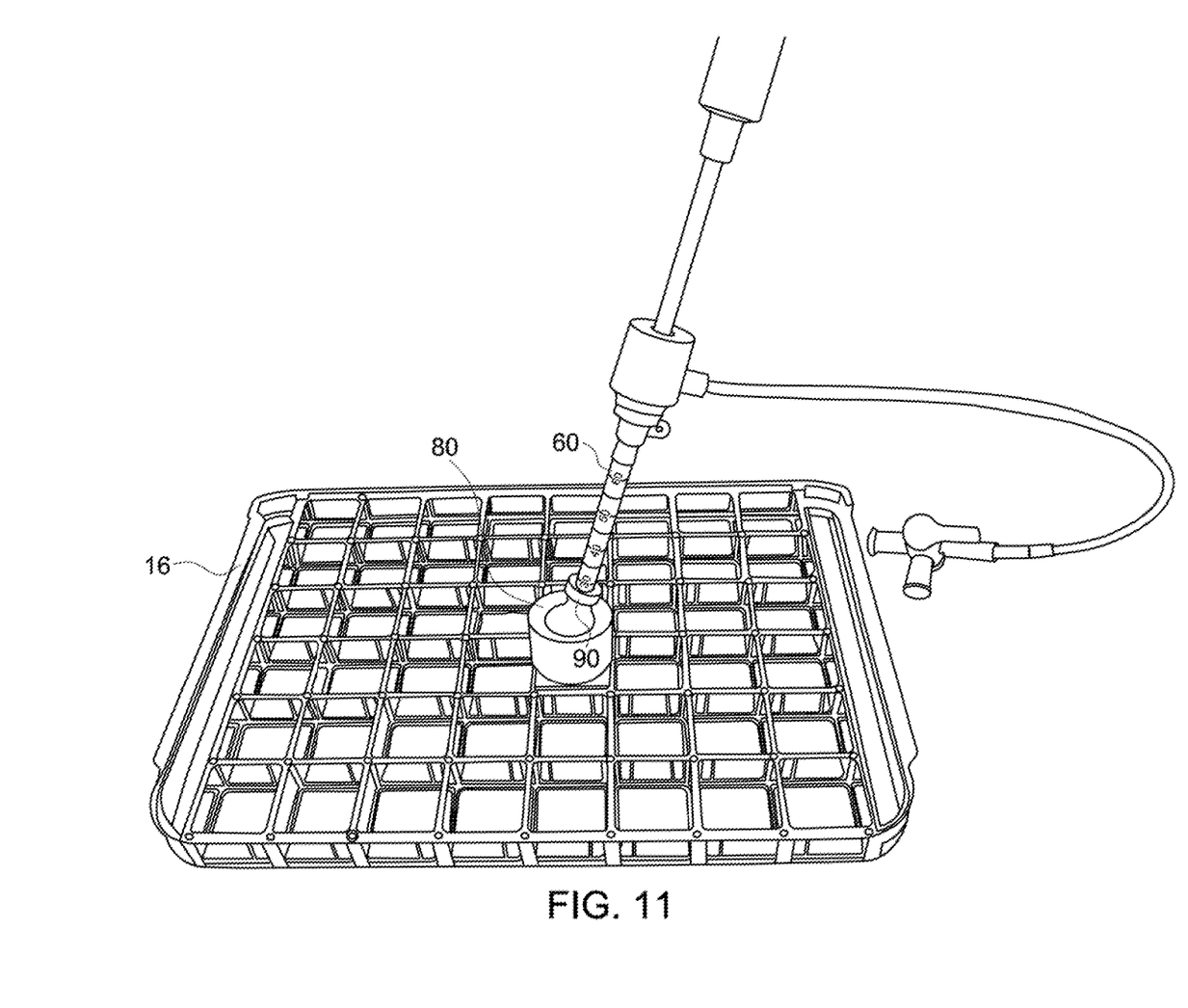
FIG. 11 depicts the adjustable grid insert of FIG. 10 in conjunction with a grid, introducer, and insertable tool, in accordance with aspects of the present disclosure.

An example of an adjustable insert 80 is shown in FIG. 11. In this example, the insert 80 has been adjusted to have the calculated orientation of the guide channel 82. The adjusted insert 80 is disposed in a specified opening of the grid 16 and an introducer and associated tool (e.g., a stylet) are inserted into the guide channel on the insert 80. A depth ring 90 is also depicted which limits the depth which the tool is inserted when the ring 90 contacts the insert 80. In this manner, the tool may be inserted to the correct depth to reach the target region.

Technical effects of the invention include a grid insert, and the use of such an insert, for a tool insertion procedure, wherein the insert may be fabricated to provide a desired, non-perpendicular, tool orientation and insertion. Further technical effects include a set of grid inserts each having different guide channel orientations and/or lengths and the selection of one of the inserts from the set based on imaging data. Additional technical effects include an adjustable grid insert, and the use of such an insert, for a tool insertion procedure that may be adjusted to provide a desired, non-perpendicular, tool orientation and insertion.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A guide insert for use in insertion of a medical tool into a patient, comprising:
   a base sized and shaped to be inserted into an opening of a grid of a medical device;
   a rotatable structure configured to fit on or within the base;
   a securing cap configured to secure the rotatable structure to the base and to prevent rotation of the rotatable structure when secured;
   wherein the rotatable structure comprises a protruding shaft defining at least a portion of a guide channel;
   wherein the rotatable structure is orientated in terms of an altitude, an azimuth, an offset and a length on the guide channel relative to the grid or the base; and
   wherein the base includes an outer ring with a plurality of struts extending from the outer ring to the guide channel.

2. The guide insert of claim 1, wherein orientation of the rotatable structure is determined by a location of a selected target region determined from a set of image data of the patient.

3. The guide insert of claim 2, wherein the rotatable structure has non-90 degrees orientation relative to the grid or the base.

4. The guide insert of claim 1, wherein at least a portion of the base comprises a hollow structure, wherein an exterior surface of the hollow structure comprises a first set of threaded grooves.

5. The guide insert of claim 4, wherein the securing cap comprises a hollow component, wherein an interior surface of the hollow component comprises a second set of threaded grooves.

6. The guide insert of claim 1, wherein the guide insert is a biopsy insert, wherein the grid is a biopsy grid.

7. The guide insert of claim 1, wherein the protruding shaft comprises a telescoping structure, wherein the telescoping structure adjusts length of the protruding shaft.

8. The guide insert of claim 1, wherein the protruding shaft is a hollow shaft, wherein an interior of the hollow shaft comprises threaded grooves.

9. The guide insert of claim 1, wherein the rotatable structure has a hole defining at least a portion of a guide channel.

10. The guide insert of claim 1, wherein the rotatable structure has a spherical structure, wherein the securing cap has a hollow cylindrical structure, and wherein a portion of the base has a cylindrical structure.

11. The guide insert of claim 1, wherein the altitude, the azimuth, and the offset are computed based on a selected lesion position within images of the patient with respect to a selected grid opening.

12. A medical device comprising:
    a plate;
    a grid disposed facing the plate;
    a medical tool;
    a guide insert positioned at least partially within an opening of a plurality of openings formed in the grid, and configured for use in insertion of the medical tool into a patient, wherein the guide insert comprises:
       a base sized and shaped to be inserted into the opening of the grid;
       a rotatable structure configured to fit on or within the base;
       a securing cap configured to secure the rotatable structure to the base and to prevent rotation of the rotatable structure when secured;
    wherein the rotatable structure comprises a protruding shaft or a hole defining at least a portion of a guide channel;
    wherein the rotatable structure is orientated in terms of an altitude, an azimuth, an offset and a length on a guide channel relative to the grid or the base; and
    wherein the base includes an outer ring with a plurality of struts extending from the outer ring to the guide channel.

13. The medical device of claim 12, wherein at least a portion of the base comprises a hollow structure, wherein an exterior surface of the hollow structure comprises a first set of threaded grooves.

14. The medical device of claim 13, wherein the securing cap comprises a hollow component, wherein an interior surface of the hollow component comprises a second set of threaded grooves.

15. A method comprising:
    receiving an indication of a selected target region within a set of image data of a patient;
    determining a grid location in a grid of a medical device for insertion of a guide insert based on the selected target region;
    determining at least a guide channel orientation for the guide insert based on the selected target region and the grid location;
    adjusting, without user intervention, a rotatable structure of the guide insert based on a determined guide channel orientation, wherein the rotatable structure defines at least a portion of a guide channel;

locking the rotatable structure to a base of the guide insert using a securing cap of the guide insert, at the determined guide channel orientation after adjusting the rotatable structure;

wherein the rotatable structure is orientated in terms of an altitude, an azimuth, an offset and a length on the guide channel relative to the grid or the base; and wherein the base includes an outer ring with a plurality of struts extending from the outer ring to the guide channel.

16. The method of claim 15, wherein the guide channel orientation has non-90 degrees orientation relative to the grid or the base.

* * * * *